United States Patent
Govari et al.

(10) Patent No.: US 10,751,164 B2
(45) Date of Patent: Aug. 25, 2020

(54) INELASTIC NOISELESS AIR BAG IN A BREAST IMPLANT

(71) Applicant: Biosense Webster (Israel) Ltd., Yokneam (IL)

(72) Inventors: Assaf Govari, Haifa (IL); Yehuda Algawi, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 21 days.

(21) Appl. No.: 15/824,000

(22) Filed: Nov. 28, 2017

(65) Prior Publication Data

US 2019/0159887 A1    May 30, 2019

(51) Int. Cl.
*A61F 2/12*    (2006.01)
*A61L 27/48*    (2006.01)
*A61L 27/26*    (2006.01)

(52) U.S. Cl.
CPC .............. *A61F 2/12* (2013.01); *A61L 27/26* (2013.01); *A61L 27/48* (2013.01); *A61F 2230/0008* (2013.01); *A61F 2240/001* (2013.01); *A61F 2250/0003* (2013.01); *A61F 2250/0018* (2013.01); *A61F 2250/0075* (2013.01); *A61L 2430/04* (2013.01)

(58) Field of Classification Search
CPC .............. A61F 2/12; A61F 2250/0003; A61F 2250/0075; A61F 2240/001; A61F 2230/0008; A61F 2250/0018; A61L 2430/04; A61L 27/48; A61L 27/26
See application file for complete search history.

(56) References Cited

U.S. PATENT DOCUMENTS

| 3,852,833 A * | 12/1974 | Koneke | A61F 2/12 55/385.5 |
|---|---|---|---|
| 4,125,117 A | 11/1978 | Lee | |
| 5,549,672 A | 8/1996 | Maddock | |
| 8,409,279 B2 | 4/2013 | Freund | |
| 8,674,035 B2 | 3/2014 | Padsalgikar | |
| 9,486,309 B2 | 11/2016 | Schuessler | |
| 2003/0166777 A1 | 9/2003 | Vachon | |
| 2006/0069403 A1 | 3/2006 | Shalon | |
| 2010/0010531 A1 | 1/2010 | Shalon | |
| 2011/0270391 A1 * | 11/2011 | Chitre | A61F 2/12 623/8 |

(Continued)

FOREIGN PATENT DOCUMENTS

EP    2247260 B1    11/2010

OTHER PUBLICATIONS

International Search Report for Application No. PCT/IB2018/058955, dated Mar. 13, 2019.

*Primary Examiner* — Brian A Dukert
*Assistant Examiner* — Rebecca Lynee Zimmerman
(74) *Attorney, Agent, or Firm* — Eugene L. Szczecina, Jr.

(57) ABSTRACT

An implantable device includes a first sealed flexible shell configured for implantation within a breast of a human subject, an elastic filler material contained within the first sealed flexible shell, and a second sealed flexible, inelastic shell, which is disposed within the elastic filler material inside the first sealed flexible shell and is inflated with a volume of gas. The second shell includes a material selected such that a root-mean-square (RMS) sound pressure caused by a deformation of the second shell not exceeding 50 mm does not exceed 20 micro-Pascals.

8 Claims, 5 Drawing Sheets

(56) References Cited

U.S. PATENT DOCUMENTS

2012/0277858 A1  11/2012  Brinon
2014/0100656 A1   4/2014  Namnoum
2016/0256295 A1   9/2016  Wollnick et al.

* cited by examiner

INELASTIC NOISELESS AIR BAG IN A BREAST IMPLANT

FIELD OF THE INVENTION

The present invention relates generally to medical devices, and particularly to breast implants.

BACKGROUND

A breast implant is either inserted in a human breast or attached on the breast in order to replace tissue that has been medically removed in an operation such as a mastectomy. The purpose of the breast implant is to restore to the breast its external form, including its tactile feel and weight. A breast implant may also be inserted in a breast to enhance or enlarge the appearance of the breast for cosmetic purposes.

U.S. Patent Applications 2006/0069403 and 2010/0010531 describe a tissue expansion device, which comprises an expandable compartment adapted for implanting in a body of a subject, and a gas source adapted for implanting in a body of a subject and operably connected to the expandable compartment for inflation by transfer of a gas into it.

U.S. Pat. No. 5,549,672 describes a method and apparatus for filling mammary prostheses and tissue expanders using pumping systems.

U.S. Pat. No. 8,409,279 describes a method for implanting a breast implant into a subject. The method includes providing a sterile, flexible, elastic biodegradable bag sized to contain the breast implant, providing a sterile breast implant, inserting, using sterile handling, the sterile breast implant into the sterile bag to form a sterile breast implant assembly, closing the bag to fully enclose the implant within the bag, and implanting in a sterile manner the sterile breast implant assembly into the subject.

U.S. Patent Application 2012/0277858 describes an implant for anatomically reconstructing, or increasing the positive displacement of, a soft portion of a living body. The implant is formed of a casing made of a flexible biocompatible material and filled with a gel.

U.S. Patent Application 2014/0100656 describes a breast implant. The disclosed implant is an inflatable device comprising an outer shell composed of a biological material and an inner chamber.

U.S. Pat. No. 8,674,035, which is incorporated herein by reference, describes a biostable polyurethane or polyurea comprising a soft segment comprising a polysiloxane, and a hard segment which is a reaction product of a diisocyanate and a linear difunctional chain extender, processes for their preparation and their use in the manufacture of biomaterials, devices, articles or implants.

U.S. Patent Application 2003/0166777, which is incorporated herein by reference, describes cured blends of silicone polymer with organic polymers, without the use of a compatibilizer.

SUMMARY

Embodiments of the present invention that are described hereinbelow provide for an improved breast implant.

There is therefore provided, in accordance with an embodiment of the present invention, an implantable device, which includes a first sealed flexible shell configured for implantation within a breast of a human subject, an elastic filler material contained within the first sealed flexible shell, and a second sealed flexible, inelastic shell, which is disposed within the elastic filler material inside the first sealed flexible shell and is inflated with a volume of gas. The second shell includes a material selected such that a root-mean-square (RMS) sound pressure caused by a deformation of the second shell not exceeding 50 mm does not exceed 20 micro-Pascals.

In an embodiment the material includes a composite of polyamide and polyurethane.

In another embodiment the elastic filler material includes silicone gel.

In a further embodiment the volume of gas includes a volume of air.

There is also provided, in accordance with an embodiment of the present invention, a method for manufacturing an implantable device, the method including providing a first sealed flexible shell configured for implantation within a breast of a human subject, filling the first sealed flexible shell with an elastic filler material, providing a second sealed flexible, inelastic shell fabricated of a material selected such that a root-mean-square (RMS) sound pressure caused by a deformation of the second shell not exceeding 50 mm does not exceed 20 micro-Pascals, inflating the second sealed flexible shell with a volume of gas, and disposing the second sealed flexible, inelastic shell within the elastic filler material inside the first sealed flexible shell.

In a further embodiment filling the first sealed flexible shell includes filling it with silicone gel.

In another embodiment inflating the second sealed flexible, inelastic shell includes inflating it with air.

The present invention will be more fully understood from the following detailed description of the embodiments thereof, taken together with the drawings in which:

DETAILED DESCRIPTION OF EMBODIMENTS

Overview

A commonly used breast implant is an implant, wherein an elastic filler material, such as silicone gel, is contained in a sealed flexible shell. However, a breast implant that is completely filled with material such as silicone gel is relatively heavy, and may cause discomfort to the wearer of the implant.

Embodiments of the present invention provide an implantable device that is used as a breast implant. The device comprises a first sealed flexible shell that is configured for implantation within a breast of a human subject. An elastic filler material is contained within the first flexible shell.

There is a second sealed flexible shell that is disposed within the elastic filler material with a volume of gas within the second shell. The second shell is fabricated of a material having the property that the sound pressure caused by a deformation of the shell does not exceed 20 micro-Pascals for a deformation not exceeding 50 mm. A sound pressure of 20 micro-Pascals is typically taken as the threshold of hearing for a human with normal hearing, so that deformation of the shell yielding a sound pressure less than this figure is noiseless.

Embodiments of the present invention that are described herein address the potential for an undesirable audible noise caused by a deformation of the second shell in a low-pressure environment, such as an airplane, by using for the second shell a material such as a polyamide/polyurethane (PA/PU) composite. PA/PU composite is both flexible and inelastic, and the noise generated by a material of this type, when it changes its shape, is below the threshold of hearing referred to above. This enables the fabrication of lightweight and noiseless breast implants.

SYSTEM DESCRIPTION

Figure 1:
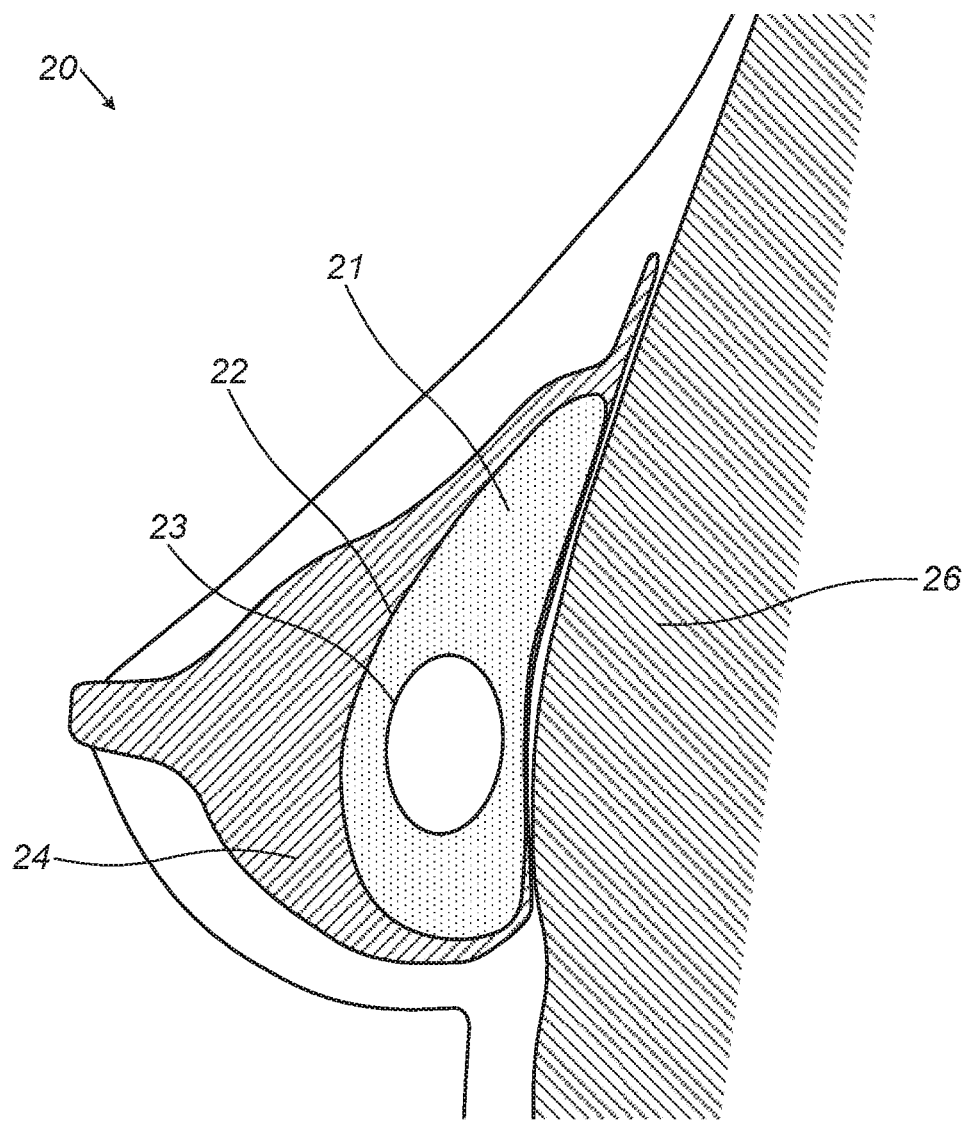
FIG. 1 is a schematic sectional illustration of a human female breast with a breast implant, in accordance with an embodiment of the invention.

FIG. 1 is a schematic sectional illustration of a human female breast 20 with a breast implant 21, in accordance with an embodiment of the present invention. Implant 21 comprises a first shell 22 and a second shell 23, described in more detail below. In the disclosed embodiment, breast implant 21 is positioned as a subglandular implant between breast tissue 24 and a pectoralis major muscle 26. In alternative embodiments, breast implant 21 may be positioned either as a subfascial, subpectoral, or submuscular implant, referring to different positions of the implant relative to pectoralis major muscle 26, as will be understood by those skilled in the art.

Figure 2:
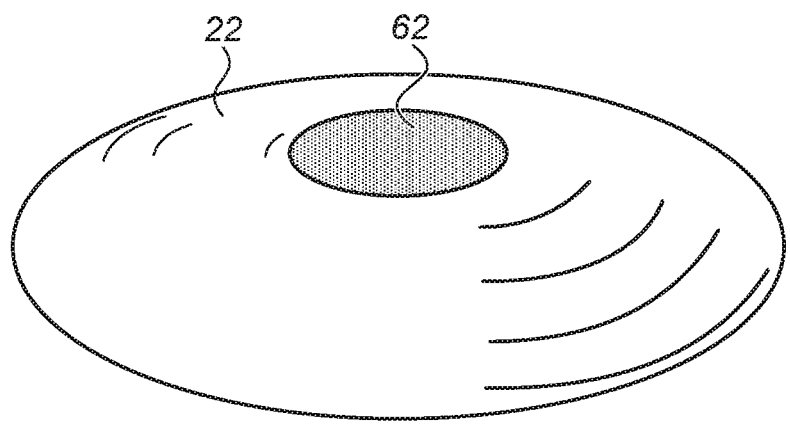
FIG. 2 is a schematic perspective view of a first shell of a breast implant, in accordance with an embodiment of the invention.

FIG. 2 is a schematic perspective view of first shell 22 of breast implant 21, in accordance with an embodiment of the invention. First shell 22 is fabricated by repeatedly dipping a mandrel (not shown) in a silicone solution. The coat of the silicone solution is allowed to solidify between consecutive dips. Once a sufficient thickness of the silicone layer covering the mandrel, typically 0.1 mm, has been reached and the silicone has solidified, the silicone "skin" is peeled off the mandrel. An opening 62 is left in first shell 22 by the stem of the mandrel.

Figure 3:
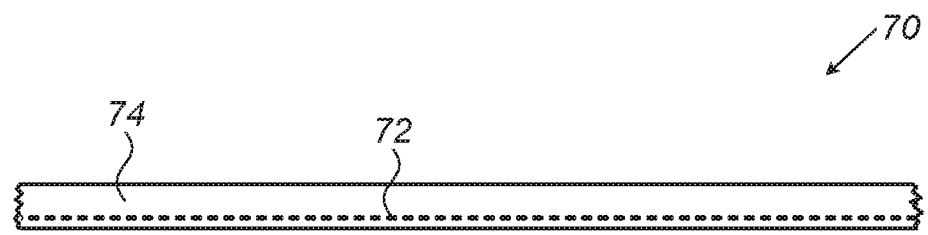
FIG. 3 is a schematic sectional view of polyamide/polyurethane (PA/PU) composite material, in accordance with an embodiment of the invention.

FIG. 3 is a schematic sectional view of a polyamide/polyurethane (PA/PU) composite material 70, in accordance with an embodiment of the invention. PA/PU composite material 70, which is a flexible, inelastic, and low-noise material, is used for second shell 23. A number of other inelastic, flexible materials exist, such as PET (polyethylene terephthalate) and nylon, but these materials produce an audible noise when deformed.

The flexibility of second shell 23 allows the shell to adapt its shape to the changing shape of implant 21 due to e.g. movement of breast 20. The inelasticity of second shell 23, due to the inelasticity of its base, which is a fine net of PA 72, prevents the shell, and thus implant 21, from changing its size in a low-pressure environment, such as inside an airplane. Both of the components of composite material 70, PA net 72 and PU 74 are flexible. The low-noise attribute of composite material 70, due to the low-noise properties of both PA net 72 and PU 74, ensures that even when second shell 23 is flexibly deformed in a low-pressure environment, the emitted sound remains below the threshold of human hearing of a human with normal hearing. The threshold of human hearing is herein assumed to be equal to a root-mean-square (RMS) sound pressure of 20 micro-Pascals. The flexible deformation expected for a breast implant does not exceed 50 mm in normal use.

Composite material 70 is fabricated by dipping fine net of PA 72 in liquid PU 74. The composite is then fed through two parallel rollers to flatten out the sheet.

Figure 4:
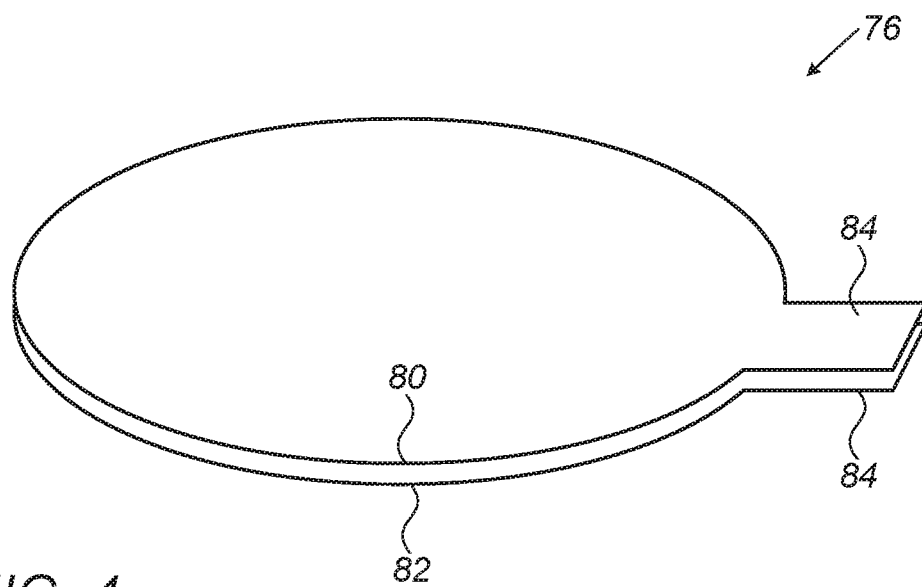
FIG. 4 is a schematic perspective view of cut PA/PU composite material prepared for radio frequency (RF) welding, in accordance with an embodiment of the invention.

FIG. 4 is a schematic perspective view of PA/PU composite material 70 after it has been cut in preparation for radio frequency (RF) welding, in accordance with an embodiment of the invention. Two similarly shaped pieces have been cut out of PA/PU composite material 70, forming an upper composite sheet 80 and a lower composite sheet 82 that together form a second shell preform 76. As described below sheets 80 and 82 are used to form second shell 23, and the shape of sheets 80 and 82 may be circular, square, or any other desired shape for second shell 23. An extension 84 is left on each part to form a fill tube 86 (shown in FIG. 5) after RF welding.

Figure 5:
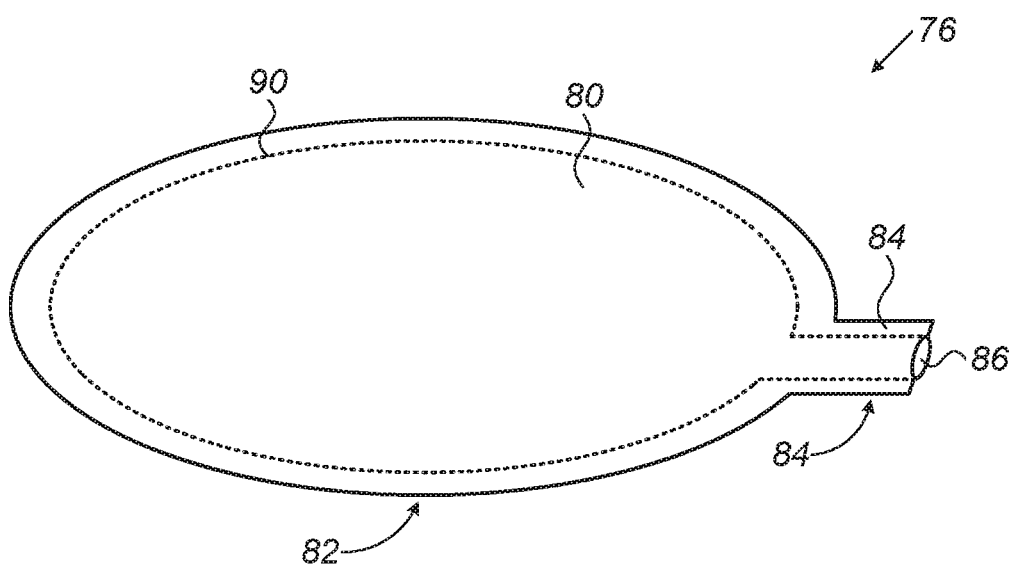
FIG. 5 is a schematic perspective view of a second shell preform after RF welding of two composite sheets, in accordance with an embodiment of the invention.

FIG. 5 is a schematic perspective view of second shell preform 76 after RF welding of upper and lower composite sheets 80 and 82, respectively, in accordance with an embodiment of the invention. Upper and lower composite sheets 80 and 82, respectively, have been RF welded together along a weld line 90 positioned at the perimeters of the sheets. In the process, a fill tube 86 has been formed from extensions 84, to be used for inflating second shell preform 76.

Figure 6:
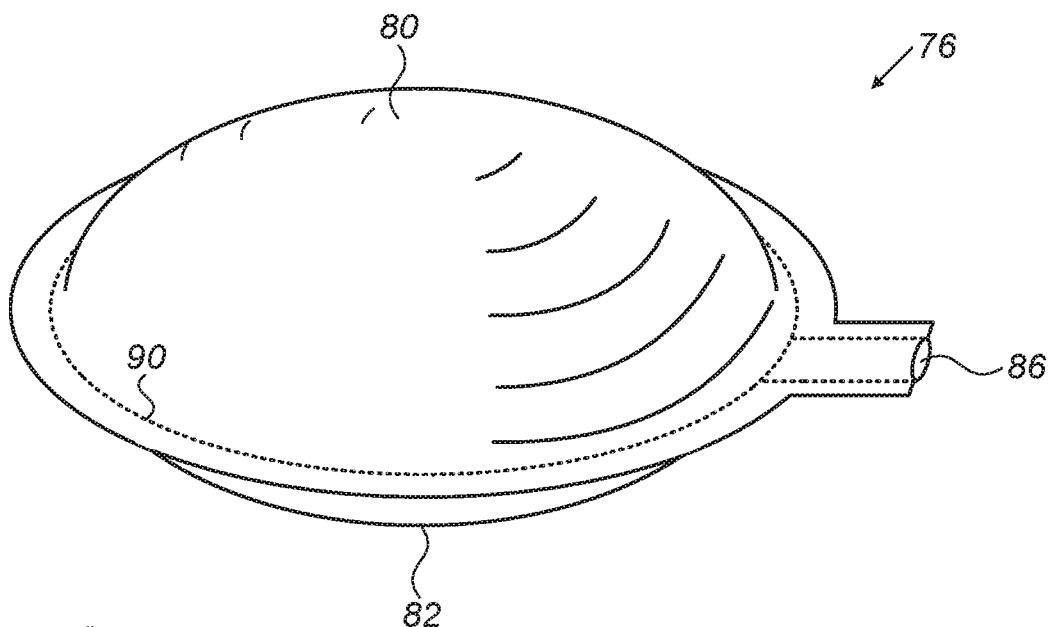
FIG. 6 is a schematic perspective view of a second shell preform after inflation, in accordance with an embodiment of the invention.

FIG. 6 is a schematic perspective view of second shell preform 76 after the preform has been inflated with air or other gas, in accordance with an embodiment of the invention. Upper and lower composite sheets 80 and 82, respectively, have formed a balloon-like volume due to the inflation of second shell preform 76 through fill tube 86.

Figure 7:
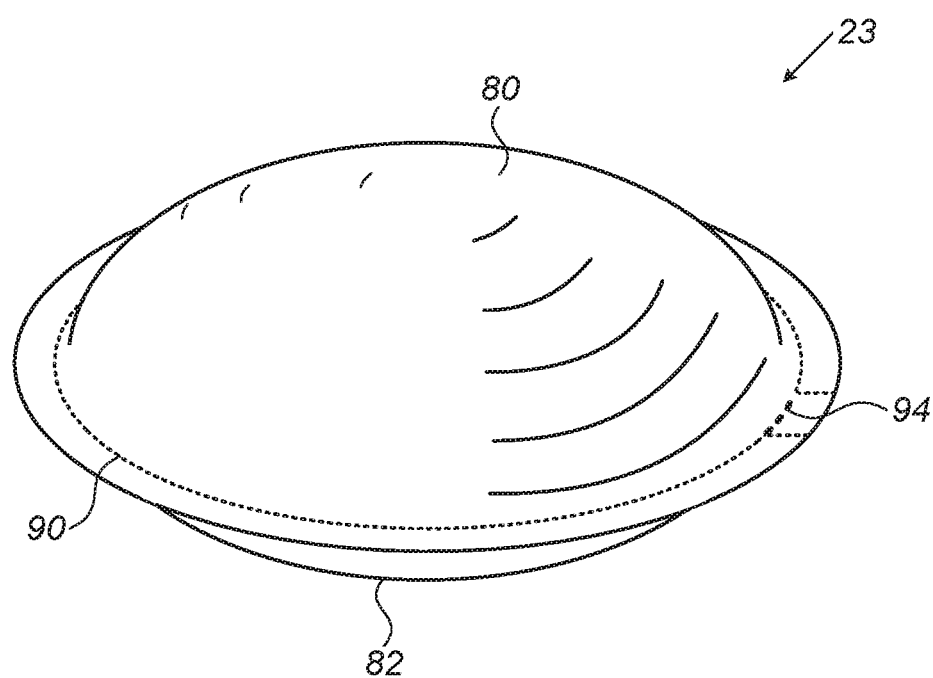
FIG. 7 is a schematic perspective view of a completed second shell, in accordance with an embodiment of the invention.

FIG. 7 is a schematic perspective view of completed second shell 23 formed from preform 76, in accordance with an embodiment of the invention. Initial RF weld 90 has been complemented with a sealing RF weld 94, thus completely sealing-off the gas volume between upper and lower composite sheets 80 and 82, respectively. In addition, the part of fill tube 86 outside the edge of second shell preform 76 has been cut off.

Figure 8:
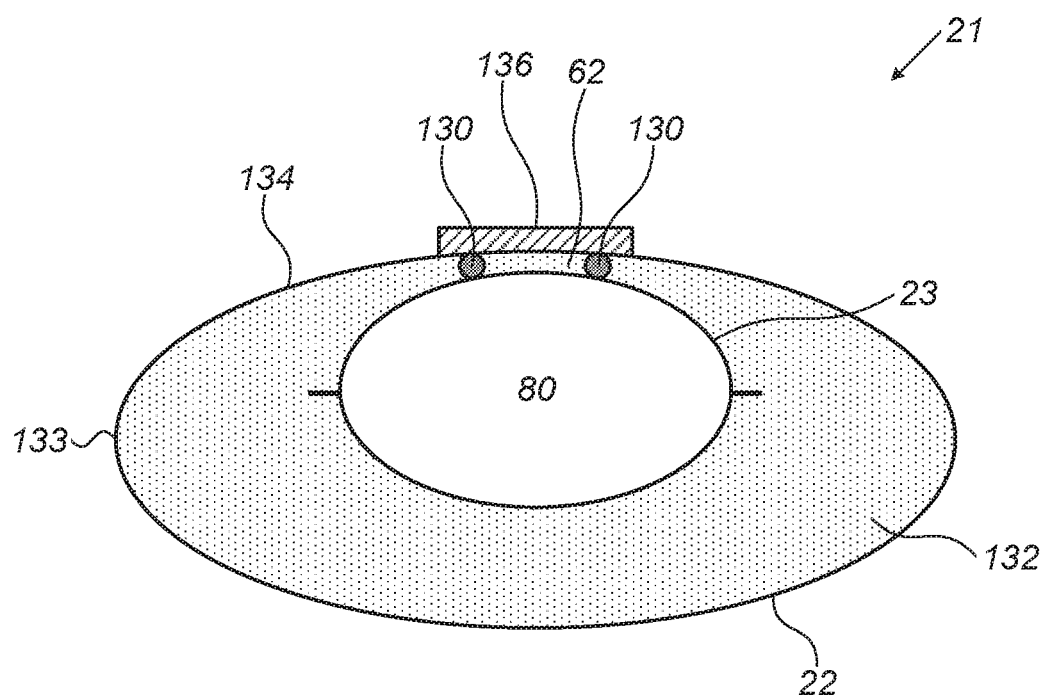
FIG. 8 is a schematic sectional view of a completed breast implant, in accordance with an embodiment of the invention.

FIG. 8 is a schematic sectional view of completed breast implant 21, in accordance with an embodiment of the invention. Completed second shell 23 (FIG. 7) has been inserted into first shell 22 (FIG. 2) through opening 62. Second shell 23 is further secured in place by a ring of cement 130, which attaches the second shell to first shell 22. Cement 130 also closes off the inside of first shell 22, thus enabling the subsequent filling of the first shell without leakage of the fill material, as will be described below. Elements 132, 133, 134, and 136 are described further below.

Figure 9:
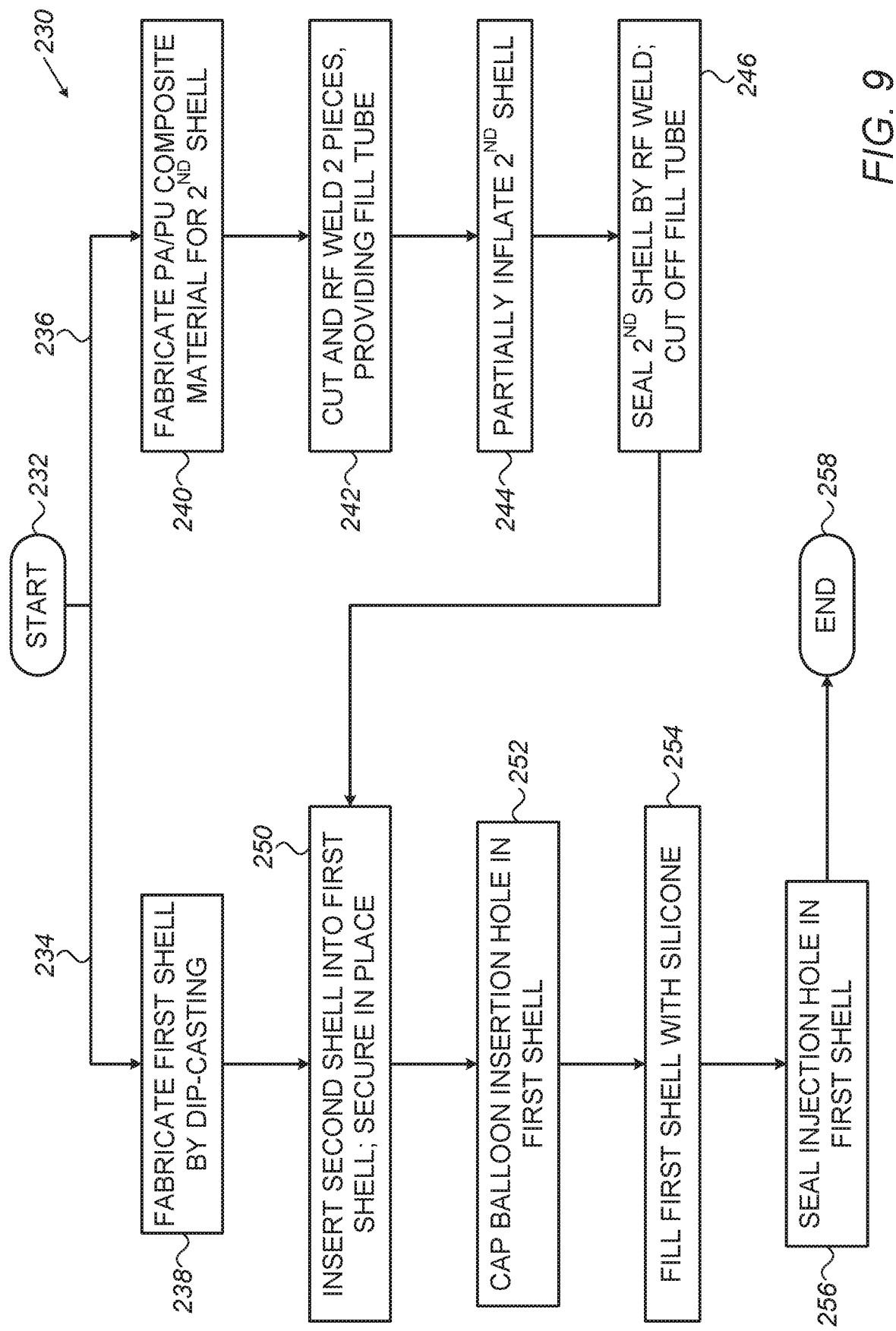
FIG. 9 is a flowchart that schematically illustrates a method for fabricating a breast implant, in accordance with an embodiment of the invention.

FIG. 9 is a flowchart 230 that schematically illustrates a method for fabricating breast implant 21, in accordance with an embodiment of the invention. The method splits into two paths 234 and 236 from a start step 232. Path 234 leads to a first shell fabricating step 238, which comprises the fabrication of first shell 22 by dip-casting as described above with reference to FIG. 2. Path 236 leads to steps 240-246 for fabricating second shell 23. In a material fabrication step 240 composite material 70 for second shell 23 is selected to be low-noise, and is fabricated as described above with reference to FIG. 3. In a cut and weld step 242, two pieces 80 and 82 of composite material 70 are cut to shape and attached to each other to form second shell preform 76 with fill tube 86 as described above with reference to FIGS. 4-5. In an inflation step 244 second shell preform 76 is inflated with gas as described above with reference to FIG. 6. In a seal step 246 inflated second shell preform 76 is sealed with an RF weld and fill tube 86 is cut off as described above with reference to FIG. 7. The result of seal step 246 is completed second shell 23.

Step 238 and steps 240-246 may be implemented serially or in parallel. These steps converge in a second shell insertion step 250, where completed second shell 23 is inserted and secured in first shell 22 as described above with reference to FIG. 8. Further referencing FIG. 8, in a cap step 252 a cap 136 of the same material as first shell 22 is used to close opening 62. The use of cap 136, in addition to cement 130, further secures implant 21 against leaks of elastic filler material 132.

In an implant fill step 254 first shell 22 is filled with an elastic filler material 132 using a syringe (not shown) through a shell wall 133 at a location 134, until a predetermined volume of material has been injected. A typical volume of breast implant 21 is 800 cc.

Elastic filler material 132 typically comprises a 2-component silicone gel. The silicone gel is a viscose liquid while being injected through the syringe. Before the silicone gel is injected into first shell 22, air bubbles are removed from the gel under vacuum. Once the silicone gel has set, typically at an elevated temperature of approximately 160° C., the injection hole at location 134 is sealed in a seal step 256 using the same material as used for fabricating first shell 22, and the construction of the breast implant terminates (in an end step 258).

Breast implant 21 is depicted in FIG. 8 as having the cross-sectional shape of an oval. However, due to the flexibility of the material of first shell 22 and completed second shell 23, as well as the elasticity of filler material 132, it will adapt its shape according to the surrounding tissue as shown in FIG. 1.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. An implantable device, comprising:
    a first sealed flexible shell configured for implantation within a breast of a human subject;
    an elastic filler material contained within the first sealed flexible shell;
    a second sealed flexible, inelastic shell, which is disposed within the elastic filler material inside the first sealed flexible shell and is inflated with a volume of gas, the second shell comprising a material selected such that a root-mean-square (RMS) sound pressure caused by a deformation of the second shell not exceeding 50 mm does not exceed 20 micro-Pascals.

2. The implantable device according to claim 1, wherein the material comprises a composite of polyamide and polyurethane.

3. The implantable device according to claim 1, wherein the elastic filler material comprises silicone gel.

4. The implantable device according to claim 1, wherein the volume of gas comprises a volume of air.

5. A method for manufacturing an implantable device, the method comprising:
    providing a first sealed flexible shell configured for implantation within a breast of a human subject;
    filling the first sealed flexible shell with an elastic filler material;
    providing a second sealed flexible, inelastic shell fabricated of a material selected such that a root-mean-square (RMS) sound pressure caused by a deformation of the second shell not exceeding 50 mm does not exceed 20 micro-Pascals;
    inflating the second sealed flexible shell with a volume of gas; and
    disposing the second sealed flexible, inelastic shell within the elastic filler material inside the first sealed flexible shell.

6. The method according to claim 5, wherein the material comprises a composite of polyamide and polyurethane.

7. The method according to claim 5, wherein filling the first sealed flexible shell comprises filling the first shell with silicone gel.

8. The method according to claim 5, wherein inflating the second sealed flexible, inelastic shell comprises inflating the second shell with air.

* * * * *